(12) United States Patent
Kim et al.

(10) Patent No.: US 10,091,654 B2
(45) Date of Patent: Oct. 2, 2018

(54) USER AUTHENTICATION METHOD AND APPARATUS

(71) Applicant: SAMSUNG ELECTRONICS CO., LTD., Suwon-si (KR)

(72) Inventors: Sang Joon Kim, Hwaseong-si (KR); Chang Soon Park, Chungju-si (KR); Jong Wook Lee, Suwon-si (KR); Seungchul Jung, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 6 days.

(21) Appl. No.: 15/241,903

(22) Filed: Aug. 19, 2016

(65) Prior Publication Data

US 2017/0180988 A1    Jun. 22, 2017

(30) Foreign Application Priority Data

Dec. 21, 2015  (KR) .................. 10-2015-0182728

(51) Int. Cl.
*H04W 12/06* (2009.01)
*A61B 5/04* (2006.01)
(Continued)

(52) U.S. Cl.
CPC ............... *H04W 12/06* (2013.01); *A61B 5/04* (2013.01); *G06F 3/03545* (2013.01);
(Continued)

(58) Field of Classification Search
CPC .. H04W 12/06; G06F 3/03545; G06F 3/0414; G06K 9/222; G06K 9/00167; G06K 9/00006; H04L 63/0861; H04M 1/7253
See application file for complete search history.

(56) References Cited

U.S. PATENT DOCUMENTS 6,307,956 B1 * 10/2001 Black .................. G06F 3/03545
382/124
8,348,538 B2    1/2013 Van Loenen et al.
(Continued)

FOREIGN PATENT DOCUMENTS

JP    2002-55768 A    2/2002
JP    2005-173809 A   6/2005
(Continued)

OTHER PUBLICATIONS

C. Hook, et al., "New Pen Device for Biometrical 3D Pressure Analysis of Handwritten Characters, Words and Signatures," Proceedings of the 2003 ACM SIGMM Workshop on Biometrics Methods and Applications, WBMA '03, Nov. 8, 2003 (8 pages in English).
(Continued)

*Primary Examiner* — Brandon J Miller
(74) *Attorney, Agent, or Firm* — NSIP Law

(57) ABSTRACT

A user authentication apparatus includes: a motion sensor configured to receive motion data associated with a motion of a body of the user authentication apparatus; a biometric sensor configured to receive biometric data associated with a user of the user authentication apparatus; and a processor configured to identify a signature of the user based on the motion data, and authenticate the user based on the identified signature and the biometric data.

25 Claims, 11 Drawing Sheets

(51) Int. Cl.
*G06F 3/0354* (2013.01)
*G06K 9/00* (2006.01)
*H04M 1/725* (2006.01)
*H04L 29/06* (2006.01)
*G06K 9/22* (2006.01)

(52) U.S. Cl.
CPC ..... *G06K 9/00006* (2013.01); *G06K 9/00167* (2013.01); *G06K 9/222* (2013.01); *H04L 63/0861* (2013.01); *H04M 1/7253* (2013.01)

(56) References Cited

U.S. PATENT DOCUMENTS

| | | | | |
|---|---|---|---|---|
| 9,119,539 | B1* | 9/2015 | Dotan | A61B 5/02438 |
| 9,576,179 | B2* | 2/2017 | Bae | G06K 9/00013 |
| 2002/0025062 | A1* | 2/2002 | Black | G06F 3/03545 |
| | | | | 382/116 |
| 2009/0074263 | A1* | 3/2009 | Higuchi | A61B 5/1172 |
| | | | | 382/126 |
| 2011/0227882 | A1 | 9/2011 | Silverbrook et al. | |
| 2012/0242603 | A1 | 9/2012 | Engelhardt et al. | |
| 2014/0149281 | A1* | 5/2014 | Shvarts | G06Q 30/06 |
| | | | | 705/39 |
| 2014/0222968 | A1 | 8/2014 | Rakan | |
| 2014/0282945 | A1* | 9/2014 | Smith | G06F 21/32 |
| | | | | 726/6 |
| 2014/0310804 | A1 | 10/2014 | Apostolos et al. | |
| 2015/0161876 | A1* | 6/2015 | Castillo | G08B 21/0453 |
| | | | | 340/539.11 |
| 2015/0242673 | A1 | 8/2015 | Singhal | |
| 2016/0078277 | A1* | 3/2016 | Sprigg | G06K 9/00174 |
| | | | | 382/119 |
| 2016/0087952 | A1* | 3/2016 | Tartz | H04W 12/06 |
| | | | | 455/411 |
| 2016/0148039 | A1* | 5/2016 | Potash | G06K 9/00885 |
| | | | | 382/119 |

FOREIGN PATENT DOCUMENTS

| | | |
|---|---|---|
| JP | 2014-27564 A | 2/2014 |
| KR | 10-1226304 B1 | 1/2013 |
| KR | 10 2013-0140439 A | 12/2013 |
| KR | 10-2014-0055507 A | 5/2014 |

OTHER PUBLICATIONS

Extended European Search Report dated May 23, 2017 in Corresponding European Application No. 16204053.9 (14 pages in English).

* cited by examiner

USER AUTHENTICATION METHOD AND APPARATUS

CROSS-REFERENCE TO RELATED APPLICATION(S)

This application claims the benefit under 35 USC § 119(a) of Korean Patent Application No. 10-2015-0182728, filed on Dec. 21, 2015, in the Korean Intellectual Property Office, the entire disclosure of which is incorporated herein by reference for all purposes.

BACKGROUND

1. Field

The following description relates to a user authentication apparatus and method.

2. Description of Related Art

Biometric data authentication technology authenticates a user by recognizing various types of biometric data. For example, biometric data of a human body may be used to verify an identity of a user in an entrance and/or exit control device and in a smart phone. Such biometric data includes, for example, a fingerprint, a vein pattern, a face, and an iris.

A contact type method or a contactless type method are used to authenticate the biometric data. The contact type method includes fingerprint authentication and vein pattern authentication, for example, and the contactless type method includes face authentication and iris authentication, for example.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a user authentication apparatus includes: a motion sensor configured to receive motion data associated with a motion of a body of the user authentication apparatus; a biometric sensor configured to receive biometric data associated with a user of the user authentication apparatus; and a processor configured to identify a signature of the user based on the motion data, and authenticate the user based on the identified signature and the biometric data.

The processor may be further configured to: verify an identity of the user based on the biometric data in response to reception of the biometric data by the motion sensor being detected; and authenticate the user based on the identified signature and the verified identity.

The motion sensor may be further configured to sense a start of a writing action of the user, and collect motion data associated with a motion corresponding to the writing action.

The motion sensor may be further configured to obtain at least one of an acceleration signal and a writing pressure signal generated with respect to the body in response to the writing action of the user. The processor may be further configured to track a motion of the body based on at least one of the acceleration signal and the writing pressure signal, and estimate the signature of the user based on the tracked motion.

The user authentication apparatus may further include a force sensor configured to sense a gripping force used to grip the body, wherein the processor is further configured to detect handwriting of the user based on at least one of the acceleration signal, the writing pressure signal, or the gripping force while the motion is being tracked.

The processor may be further configured to: estimate a writing posture based on at least one of a gripping force applied by the user to grip the body, a writing pressure, or a fingerprint image; and authenticate the user further based on the writing posture.

The biometric sensor may be further configured to sense a biometric signal waveform from the user. The processor may be further configured to detect a motion artifact associated with writing from the biometric signal waveform, and authenticate the user further based on the detected motion artifact.

The biometric sensor may be further configured to receive a fingerprint image from the user. The processor may be further configured to extract distortion information of the fingerprint image from the fingerprint image, and authenticate the user further based on the extracted distortion information.

The biometric sensor may be further configured to sense a biometric signal waveform including at least one of an electrocardiogram (ECG) signal or a photoplethysmograph (PPG) signal. The processor may be further configured to verify an identity of the user based on the sensed biometric signal waveform, and authenticate the user further based on the verified identity.

The biometric sensor may be further configured to measure an electrocardiogram (ECG) signal using an external biometric sensor and the biometric sensor in response a contact between the external biometric sensor and the body being sensed. The processor may be further configured to verify an identity of the user based on the measured ECG signal, and authenticate the user further based on the verified identity.

The biometric sensor may be further configured to receive a fingerprint image from the user. The processor may be configured to authenticate the user further based on the received fingerprint image and the signature in response to reception of the fingerprint image by the biometric sensor being detected.

The user authentication apparatus may further include a communicator configured to communicate with an external authentication device, and the processor may be further configured to receive identification information associated with at least one of a body part or a voice of the user from the external authentication device through the communicator in response to the external authentication device being available, and authenticate the user further based on the received identification information.

The user authentication apparatus may further include a communicator configured to receive at least one of a face image or voice data from an external authentication device, and the processor may be configured to authenticate the user further based on at least one of the face image or the voice data.

The processor may be further configured to apply a weight to at least one of an identification result obtained based on the signature, an identification result obtained based on the biometric data, or an identification result obtained by an external authentication device, and authenticate the user further based on the at least one identification result having the weight applied thereto.

The processor may be further configured to determine the weight with respect to each of the identification results based on accuracies of the signature, the biometric data, or a signal received from the external authentication device.

According to another general aspect, a user authentication method includes: receiving motion data associated with a motion of a body of a user authentication apparatus; receiving biometric data associated with a user of the authentication apparatus; identifying a signature of the user based on the motion data; and authenticating the user based on the identified signature and the biometric data.

A non-transitory computer-readable storage medium may include programmed instructions configured to cause a computer to perform the method.

In another general aspect, a user authentication apparatus includes: a motion sensor configured to track a motion of the user authentication apparatus; and a processor configured to detect a handwriting feature while the motion is being tracked, identify a signature of a user of the user authentication apparatus based on the tracked motion, and authenticate the user based on the identified signature and the detected handwriting feature.

The processor may be further configured to detect the handwriting feature based on at least one of an acceleration of the user authentication apparatus, a writing pressure, a gripping force applied by the user to grip the user authentication apparatus, or biometric data of the user.

The processor may be further configured to: estimate at least a portion of the signature while tracking the motion in real time; and authenticate the user by comparing the portion of the signature to a corresponding portion of an enrolled signature stored in a database.

In another general aspect, a writing instrument includes: a motion sensor configured to receive motion data associated with a motion of a body of the writing instrument while a user performs a writing action with the writing instrument; a pressure sensor configured to detect a writing pressure signal generated in response to the writing action; and a processor configured to identify a signature of the user based on the motion data and the writing pressure signal, and authenticate the user based on the identified signature.

The detecting of the writing pressure signal may include detecting a point at which a predetermined writing pressure is applied.

The processor may be further configured to distinguish the identified signature from another signature having a form that is similar to a form of the identified signature, based on the detecting of the point at which the predetermined pressure is applied.

The processor may be further configured to identify the user based on biometric data received from a biometric sensor.

Other features and aspects will be apparent from the following detailed description, the drawings, and the claims.

Figure 1:
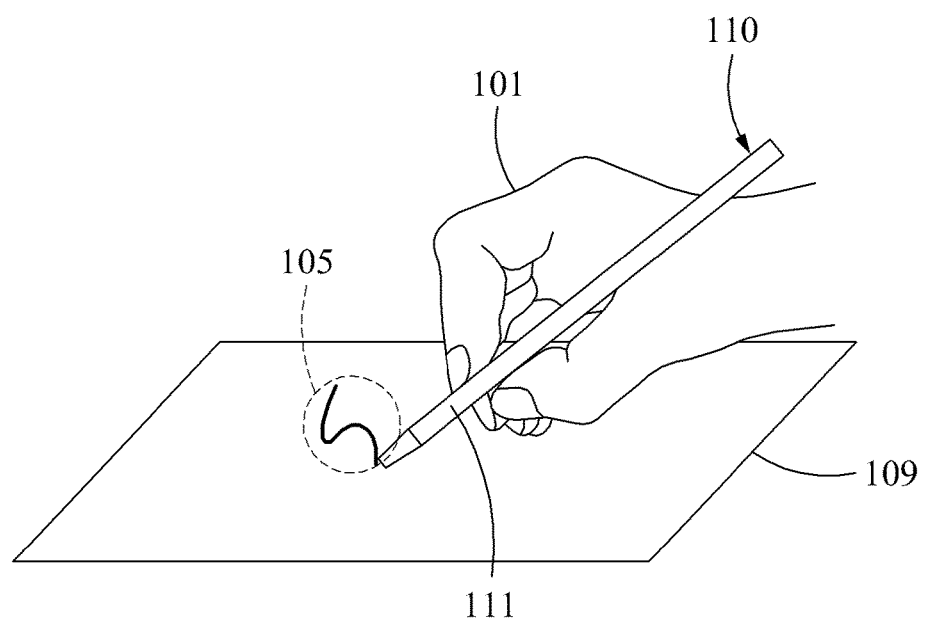
FIG. 1 illustrates an example of a user authentication apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "include/comprise" and/or "have" when used in this specification, specify the presence of stated features, integers, steps, operations, elements, components, and/or combinations thereof, but do not preclude the presence or addition of one or more other features, numbers, steps, operations, elements, components, and/or groups thereof.

FIG. 1 illustrates an example of a user authentication apparatus 110. The user authentication apparatus 110 authenticates a signature 105 corresponding to a writing action of a user. For example, the user authentication apparatus 110 identifies the signature 105 corresponding to the writing action, and authenticates the user based on the identified signature 105.

Herein, the term "identification" refers to an operation of extracting a predetermined type of information based on collected or input data. The term "authentication" refers to an operation of determining whether information extracted from input data corresponds to enrolled information. For example, the user authentication apparatus 110 identifies the signature 105 by extracting the signature 105 from data collected in response to the writing action. The collected data includes, for example, an acceleration signal and a pen pressure signal. Further, the user authentication apparatus 110 authenticates the user based on the signature 105 by determining whether the identified signature 105 is enrolled in a database, for example, whether a signature having a similarity greater than or equal to a threshold, among signatures enrolled in the database, is present. For example, in response to determination that the signature 105 is enrolled in the database, the user authentication apparatus 110 authenticates the user by determining that the user corresponds to an enrolled user. In addition, the user authentication apparatus 110 authenticates the user by identifying the signature 105 and biometric data.

A writing action is a user action of writing content, such as predetermined content, using an object, and includes, for example, user actions of writing letters, writing sentences, and making a drawing. In detail, the user grips a body 111 of the user authentication apparatus 110 with a body part of the user, for example, a hand 101, and manipulates the body 111 such that a writing end of the gripped body 111, for example, a portion corresponding to a pen tip, may form a trajectory corresponding to a predetermined letter or drawing. In an example, the user authentication apparatus 110 senses a writing action of the user by tracking the trajectory formed while the writing end of the body 111 is touching a plane such as a piece of paper 109, a touch screen, a surface of a predetermined object, a curved surface, or a flat surface, for example. However, a plane, area or space for receiving a touch input of the end of the body 111 are not limited to the foregoing examples. The user authentication apparatus 110 may be designed to track a trajectory formed by the writing end of the body 111 within a predetermined distance from a predetermined plane, or track a trajectory formed by the writing end of the body 111 within a predetermined space. Furthermore, the tracked trajectory is not limited to a two-dimensional (2D) trajectory, and a three-dimensional (3D) trajectory may be tracked. In addition, the trajectory may be a single continuous trajectory. However, the trajectory is not limited to a single continuous trajectory, and may be a set of a non-continuous trajectories.

The signature 105 is, for example, an indication representing an identity of an individual. For example, the signature 105 is designated as one of a letter, a sentence, and a drawing formed in response to the writing action of the user, or a combination of at least two thereof. In an example, the signature 105 is used to verify a unique identity of the user.

In FIG. 1, the trajectory formed on the paper 109 by the writing end of the body 111 of the user authentication apparatus 110 forms the signature 105. For example, the user authentication apparatus 110 identifies the signature 105 from the trajectory formed by the writing end of the body 111 in response to the writing action. Identification of the signature 105, according to an example, will be described in detail with reference to FIG. 8.

Figure 2:
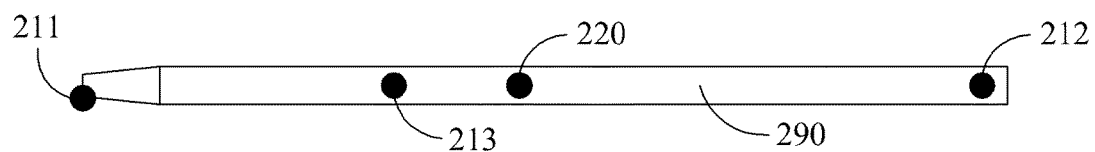
FIG. 2 illustrates an example of a user authentication apparatus.

FIG. 2 illustrates an example of a user authentication apparatus 200. A variety of sensors are provided in a body 290 of the user authentication apparatus 200. For example, referring to FIG. 2, a pen pressure sensor, or writing pressure sensor 211, a motion sensor 212, a force sensor 213, and a biometric sensor 220 are embedded in the body 290.

The body 290 of the user authentication apparatus 200 is provided in a form with which a user writes predetermined content. Various forms of a writing or drawing instrument, for example, a pen, a pencil, a stylus pen, or a brush, to be gripped by the user, may be used. The forms may include an elongated form, for example, a chopstick, to be gripped with a hand of the user. A writing end of the body 290 of the user authentication apparatus 200 may be provided in a sharp form, and the user performs a writing action by contacting a surface, such as a planar surface, with the writing end of the body 290.

The pen pressure sensor 211 senses a pen pressure, or writing pressure, applied when the user writes with the body 290. The pen pressure is, for example, a pressure applied to a plane through the body 290 while the user is performing the writing action on the surface. The pen pressure sensor 211 is disposed at the writing end of the body 290 to sense the pen pressure by measuring a pressure applied to the plane by the writing end of the body 290.

The motion sensor 212 senses a motion of the body 290 performed when the user writes with the body 290. The motion of the body 290 includes a change in position of the body 290 and a change in posture of the body 290, for example, a change in inclination formed by a central line of the body 290 with respect to the plane on which the writing action is performed. For example, as shown in FIG. 2, the motion sensor 212 is an acceleration sensor provided at another end distinct from the writing end of the body 290, for example, a tail portion of the pen, to measure an acceleration. The posture of the body 290 referenced herein denotes the inclination of the body 290 with respect to the, for example, plane on which the writing action is performed, for example, the inclination of the central line of the body 290 with respect to the plane. The central line of the body 290 corresponds to a straight line penetrating through a center of gravity of the body 290.

The force sensor 213 senses a gripping force used to grip the body 290 when the user writes with the body 290. For example, the force sensor 213 senses a force applied to at least a portion of the body 290 by a body part of the user. As shown in FIG. 2, the force sensor 213 is disposed at a portion at which a body part of the user, for example, a finger, touches the body 290 when the user grips the body 290.

The biometric sensor 220 measures biometric data of the user. The biometric data includes data indicating various biometric features such as one or more of an electrocardiogram (ECG) signal, a photoplethysmograph (PPG) signal, a fingerprint image, a face image, or a voice signal, for example.

FIG. 2 illustrates an example configuration of a user authentication apparatus. Various other configurations of user authentication apparatuses will be described with reference to FIGS. 3, 4, and 5.

Figure 3:
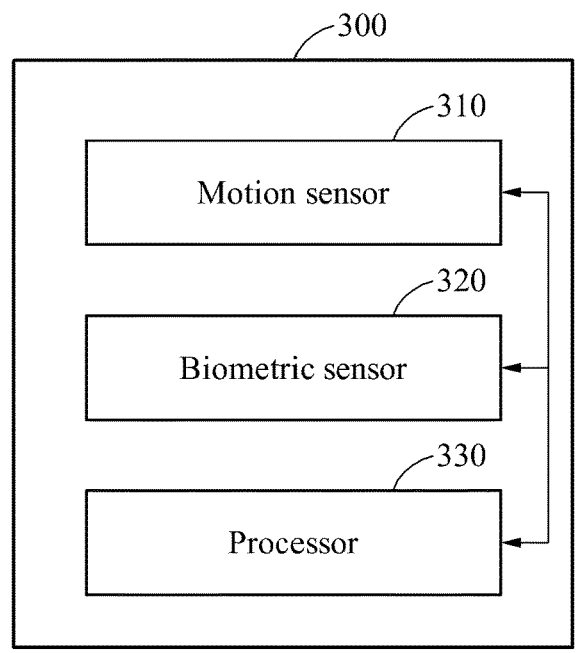
FIGS. 3, 4, and 5 are block diagrams illustrating respective examples of a user authentication apparatus.
Figure 4:
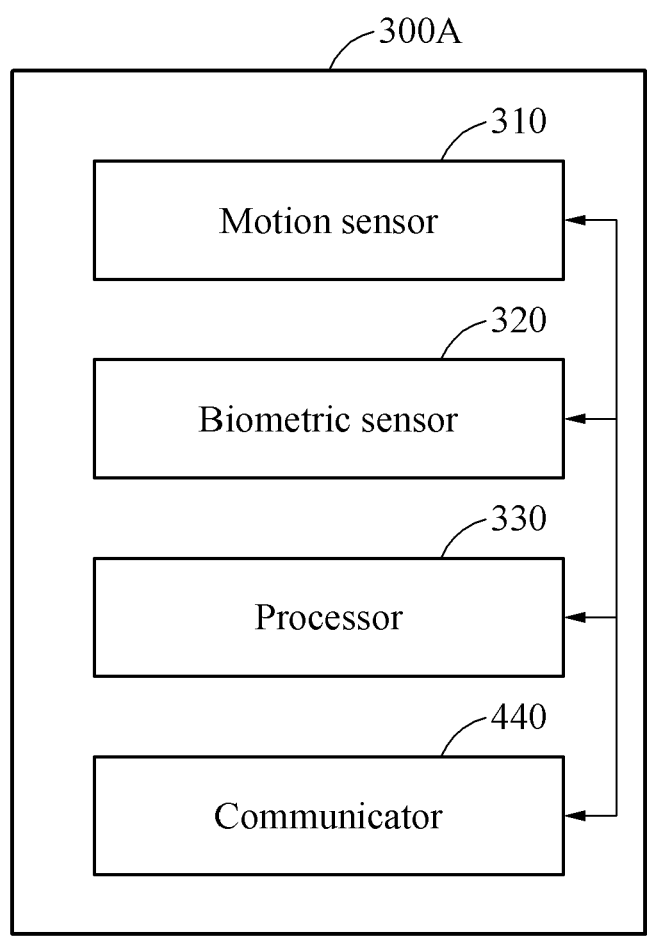
Figure 5:
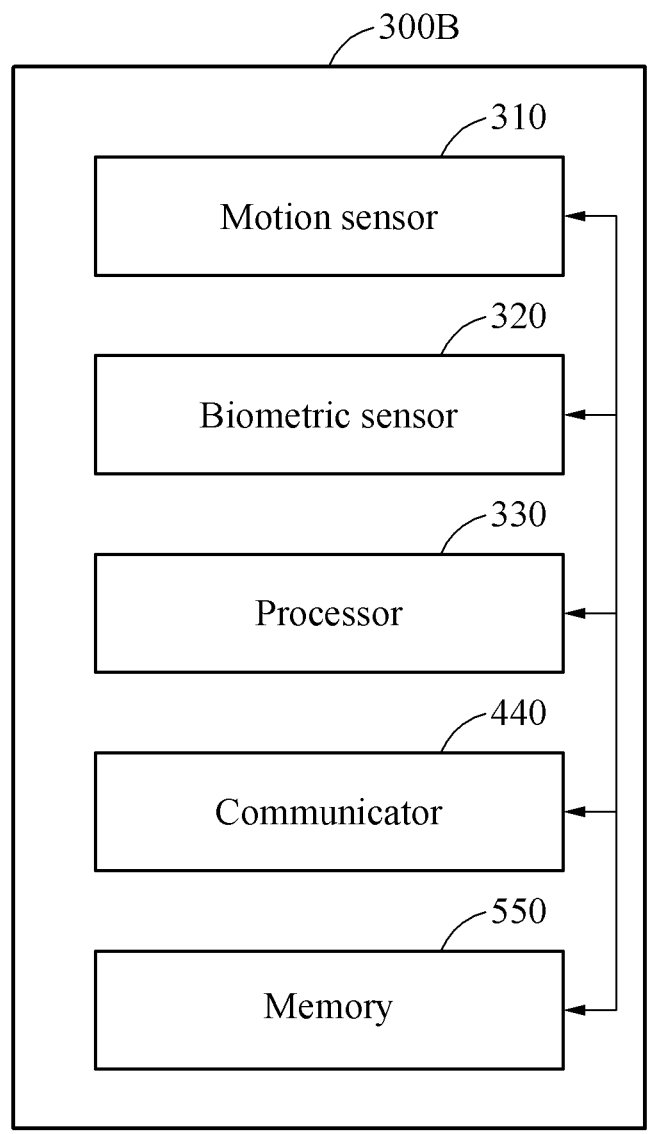

FIGS. 3 through 5 are block diagrams illustrating examples of user authentication apparatuses 300, 300A and 300B. Referring to FIG. 3, the user authentication apparatus 300 includes a motion sensor 310, a biometric sensor 320, and a processor 330. The motion sensor 310 receives motion data associated with a motion of a body of the user authentication apparatus 300. The motion sensor 310 includes, for example, an acceleration sensor, and a pen pressure sensor. The motion data is data associated with the motion of the body, and includes, for example, an acceleration signal and a pen pressure signal. The acceleration signal indicates an acceleration with respect to an n-dimensional direction, n being an integer greater than or equal to "2". The pen pressure signal indicates a pen pressure applied to a plane or other writing surface by the body of the apparatus 300.

For example, the user authentication apparatus 300 dynamically authenticates both a completely written signature and a portion of a signature being written using the embedded motion sensor 310 based on the motion of the body of the apparatus 300 and the pen pressure applied during the writing process.

The biometric sensor 320 receives biometric data associated with the user. The biometric data is data associated with a body of the user, and represents data associated with a body part of the user and a signal waveform indicating biometric features. For example, the biometric data includes one or more of an ECG signal, a PPG signal, a fingerprint image, a face image, or a voice signal, as described above.

When a user performs a signing or signature action ("signs") with the user authentication apparatus 300, the body of the user authentication apparatus 300 is essentially gripped by the user. Thus, the user authentication apparatus 300 performs biometric identification while being gripped. For example, the user authentication apparatus 300 performs pulse wave identification using a PPG signal of a finger received through the biometric sensor 320, and fingerprint identification using a fingerprint of a fingertip simultaneously with gripping.

The processor 330 identifies a signature of the user based on the motion data, and authenticates the user based on the identified signature and the biometric data. For example, the processor 330 determines whether the user corresponds to an enrolled user based on the identified signature and the biometric data.

As shown in FIG. 4, the user authentication apparatus 300A is similar to the user authentication apparatus 300, but further includes a communicator 440. The communicator 440 communicates with an external authentication device. For example, the communicator 440 attempts to communicate with the external authentication device, and receives information regarding whether the external authentication device is available, biometric data collected by the external authentication device, and identification information obtained by the external authentication device. In an example, the external authentication device is an authentication apparatus independent from the user authentication apparatus 300. The external authentication device obtains data associated with at least one of a body part and a voice of the user, for example, a face image and voice data, and generates identification information corresponding to a result of verifying an identity of the user based on the obtained data.

As shown in FIG. 5, the user authentication apparatus 300B is similar to the user authentication apparatus 300A, but further includes a memory 550. The memory 550 is configured to store a variety of data to be used to authenticate a user. For example, the memory 550 permanently or temporarily stores data to be used for user authentication. The memory 550 stores a database corresponding to an enrolled user as data to be used for user authentication. For example, the database corresponding to the enrolled user includes an enrolled signature and enrolled biometric data of the enrolled user. However, the database is not limited to including such data. The database may further include a handwriting feature of the enrolled signature, for example, handwriting of the enrolled signature, as information associated with the enrolled signature, and a biometric feature of the enrolled biometric data, for example, minutiae of a fingerprint image, as information associated with the enrolled biometric data. In an example, the memory 550 may also store a computer program to cause a computer to perform a user authentication method.

The user authentication apparatuses 300, 300A and 300B may provide an intuitive user experience (UX) using signature-based authentication while having a sufficiently small form factor using a pen-type body. Further, the user authentication apparatuses 300, 300A and 300B may achieve a higher security level by applying an additional biometric authentication scheme based on a physical contact occurring when the user authentication apparatuses 300, 300A and 300B are gripped. This may be an improvement over previous computer technologies that are specifically implemented to perform authentication operations, which do not provide sufficiently high security levels, do not provide intuitive user experiences, and are not implementable in small form factors.

Similarly, the user authentication apparatuses 300, 300A and 300B may increase performance for extracting a feature point of a signature based on unique handwriting features of each individual user, and security performance through biometric identification, again, improving on previous computer technologies. The user authentication apparatuses 300A and 300B may perform additional identification through interoperation with a neighboring external authentication device through a wireless communication function. When a user intuitively signs, the user authentication apparatuses 300, 300A and 300B secure a desired security level and authentication accuracy comprehensively using various identification schemes, as described above.

Figure 6:
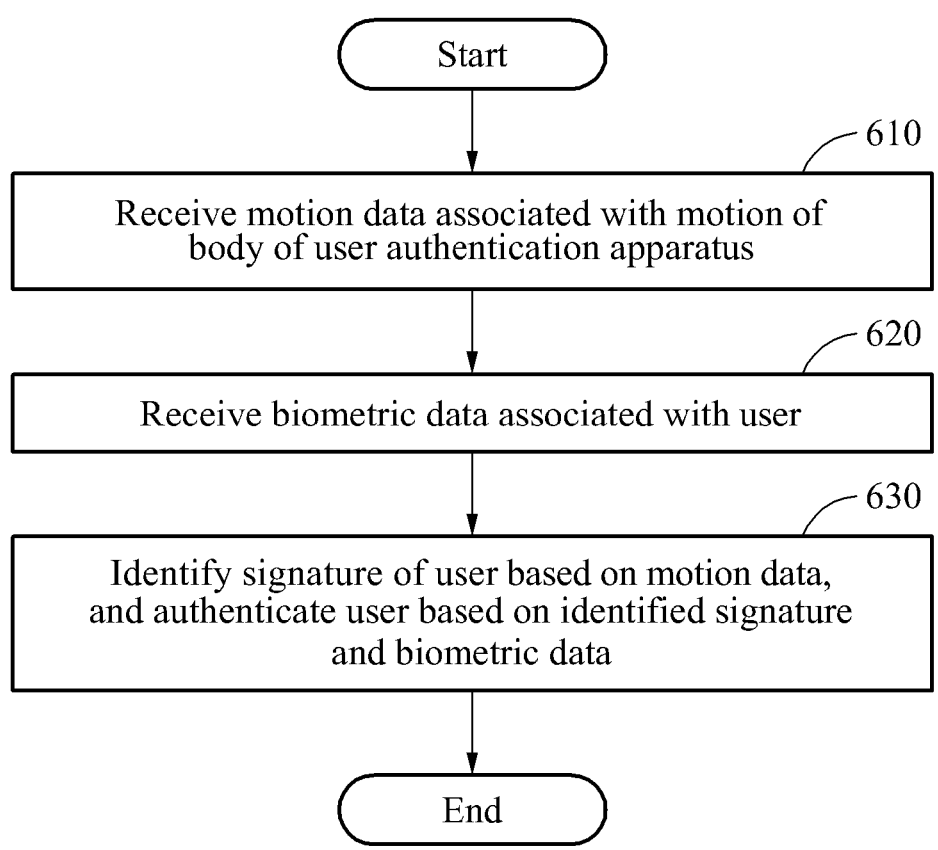
FIGS. 6 and 7 are flowcharts illustrating respective examples of a user authentication method.

FIG. 6 is a brief flowchart illustrating an example of a user authentication method. Referring to FIG. 6, in operation 610, a motion sensor of a user authentication apparatus receives motion data associated with a motion of a body of the user authentication apparatus. For example, the motion sensor measures an acceleration signal and a pen pressure signal, as described above.

In operation 620, a biometric sensor of the user authentication apparatus receives biometric data associated with a user. For example, the biometric sensor measures a signal waveform associated with a body of the user, for example, an ECG signal and/or a PPG signal, or acquires an image of a body part of the user, for example, a fingerprint, a face, and/or an iris, as described above.

In operation 630, a processor of the user authentication apparatus identifies a signature of the user based on the motion data, and authenticates the user based on the identified signature and the biometric data. For example, the processor verifies whether the user corresponds to an enrolled user by determining whether the signature and the biometric data of the user match or are similar to an enrolled signature and enrolled biometric data stored in a database, as described above.

Figure 7:
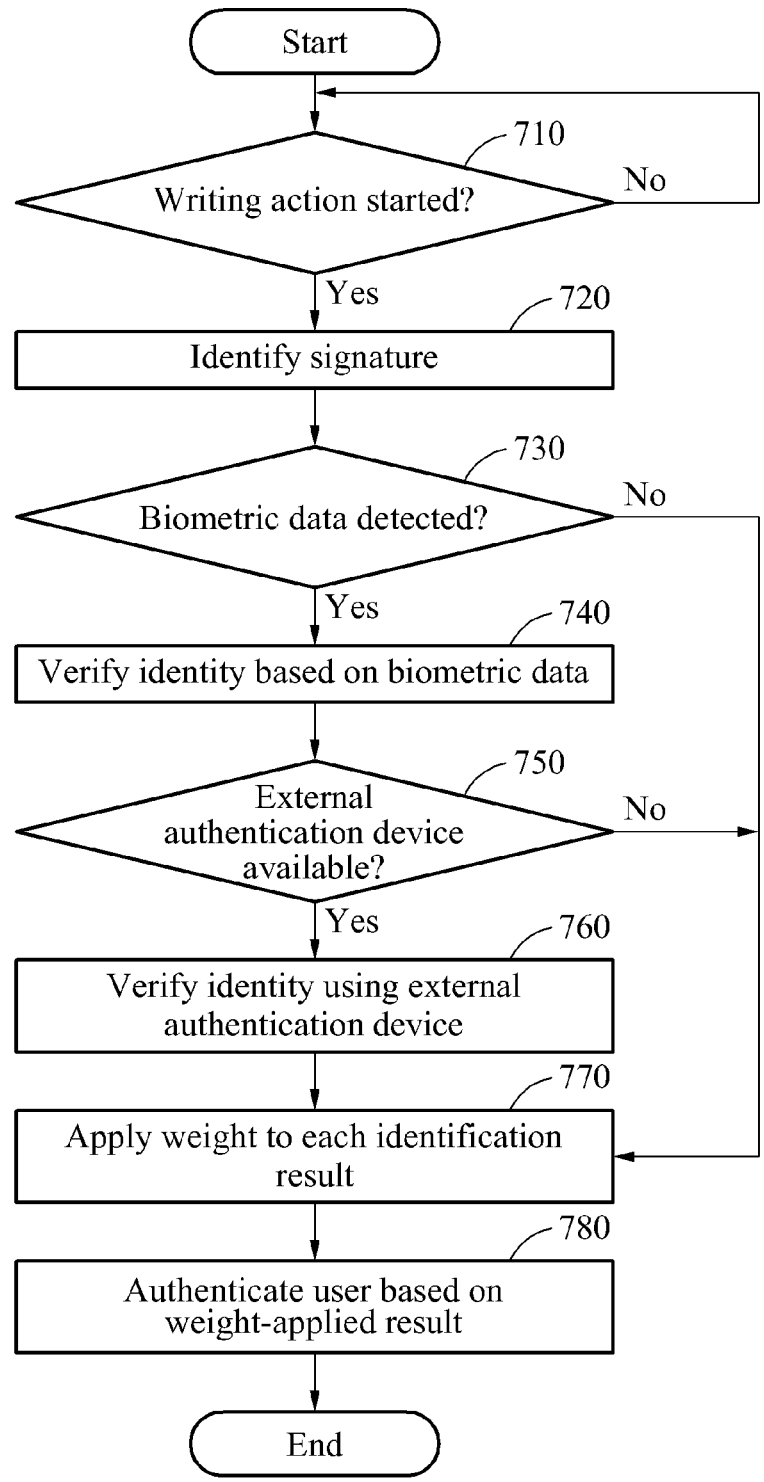

FIG. 7 is a detailed flowchart illustrating an example of a user authentication method in more detail. Referring to FIG. 7, in operation 710, a processor of the user authentication apparatus determines whether a writing action is started. The processor maintains a standby state in response to the start of the writing action not being detected. In response to the start of the writing action being detected, the processor performs operation 720. For example, the processor determines that the writing action is started in response to a pen pressure signal being sensed by a pen pressure sensor. In another example, in a case in which the user authentication apparatus includes an acoustic sensor, for example, a microphone, the processor determines that the writing action is started in response to a frictional sound between the body and a plane or surface being detected by the acoustic sensor.

In operation 720, the processor identifies a signature. For example, a motion sensor collects motion data associated with a motion corresponding to the writing action in response to the start of the writing action of the user being sensed. The processor identifies the signature based on the collected motion data.

In operation 730, the processor determines whether biometric data is detected. For example, the processor determines whether the biometric data is received by a biometric sensor. In the example of FIG. 7, in response to the biometric data not being detected, the processor authenticates the user based on only the signature through operations 770 and 780. However, examples are not limited to the foregoing sequence of operations 730, 770 and 780. In another example, although the biometric data is not detected in operation 730, the processor may perform operation 750 after performing operation 730 in response to an external authentication device being available.

In operation 740, the processor verifies an identity of the user based on the biometric data in response to reception of the biometric data being detected in operation 730.

In operation 750, the processor determines whether an external authentication device is available. For example, the processor receives information regarding whether the external authentication device is available from the external authentication device through a communicator. In response to the external authentication device being available, the processor performs operation 760. In response to the external authentication device being unavailable, the processor authenticates the user based on the signature and the biometric data, in operations 770 and 780.

In operation 760, the processor verifies an identity of the user using the external authentication device. For example, the processor receives identification information associated with at least one of a body part and/or a voice of the user from the external authentication device through the communicator in response to the external authentication device being available. In this example, the processor authenticates the user based on the received identification information and the identified signature in operations 770 and 780. The identification information is identification-associated information of the external authentication device, and includes the identity of the user verified by the external authentication device, information related to a similarity of corresponding identification, for example, a similarity between information collected by the external authentication device and enrolled information.

In another example, the communicator receives at least one of a face image or voice data from the external authentication device, and the processor verifies the identity of the user based on at least one of the face image or the voice data. The processor authenticates the user further based on at least one of the face image or the voice data in operations 770 and 780.

In operation 770, the processor applies a weight to each identification result. For example, the processor applies the weight to at least one of an identification result obtained based on the signature, an identification result obtained based on the biometric data, or an identification result obtained by the external authentication device. Each identification result includes an enrolled user corresponding to an enrolled signature and enrolled biometric data having highest similarities with the collected signature and the collected biometric data in a database, and a similarity with respect to the corresponding enrolled user. The similarity refers to a level of the collected information, for example, the signature and the biometric data, being similar to the enrolled information, for example, the enrolled signature and the enrolled biometric data. As an example, similarity may be expressed by a similarity probability in which a similarity close to "0" indicates that the collected information is not similar to the enrolled information, and a similarity close to "1" indicates that the collected information is similar to the enrolled information.

The processor determines the weight with respect to each of the identification results based on accuracies of the signature, the biometric data, and a signal received from the external authentication device. For example, when an accuracy of a predetermined identification result is relatively high, the processor assigns a relatively high weight to the corresponding identification result. Conversely, as the accuracy of the predetermined identification result is relatively low, the processor assigns a relatively low weight to the corresponding identification result.

For example, the processor determines the accuracy based on a ratio of a portion of handwriting corresponding to the signature to a portion of the handwriting not corresponding to the signature, with respect to the signature identified based on the motion data. In this example, the handwriting is estimated based on the collected motion data. In another example, the processor determines the accuracy of each of the biometric data and the signal received from the external authentication device based on a signal-to-noise ratio (SNR).

In operation 780, the processor authenticates the user based on a result of applying the weight. For example, the processor authenticates the user based on the weight-applied at least one identification result. The processor determines the weight based on an identification reliability, for example, the SNR, in an individual identification process, and extracts a final complex identification level value based on the determined weight. The processor determines whether authentication succeeds based on a result of comparing the final complex identification level value to a predetermined threshold reliability, as demonstrated below in Equation 1, for example.

$$X = a_1 x_1 + a_2 x_2 + \ldots + a_n x_n \quad \text{[Equation 1]}$$

In Equation 1, $x_i$ denotes an individual identification level value corresponding to an individual identification process, and $a_i$ denotes an individual identification reliability determined based on an SNR in an individual identification process. $x_i$ and $a_i$ are normalized to values ranging between "0" and "1". Accordingly, the final complex identification level value X is deduced based on $x_i$ and $a_i$. A vector x is a vector representing a set of individual identification level values, and a vector "a" is a vector representing a set of individual identification reliabilities. In this example, Equation 1 is defined as expressing an inner product between the vector x and the vector a.

The processor may finally determine whether authentication has succeeded by comparing the final complex identification level value X calculated using Equation 1 to a determined threshold reliability $X_{TH}$, as demonstrated in the below Equation 2, for example.

$$X \gtrless X_{TH} \quad \text{[Equation 2]}$$

For example, the processor finally determines that authentication has succeeded in response to the final complex identification level value X being greater than the threshold reliability $X_{TH}$.

Figure 8:
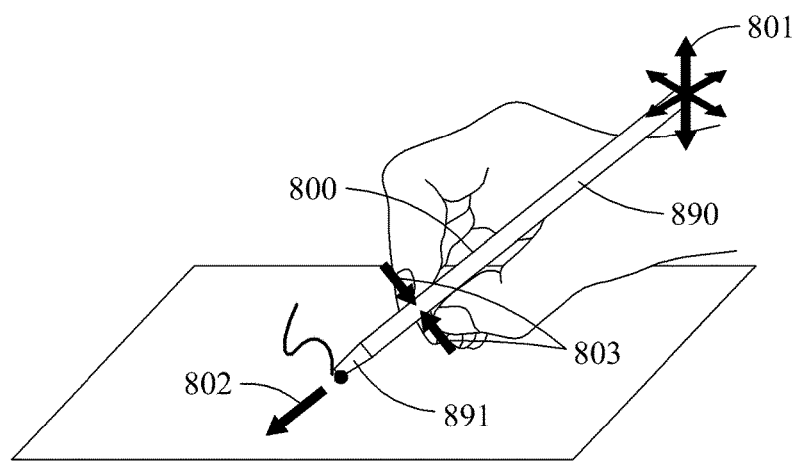
FIG. 8 illustrates an example of a use of motion data in a user authentication apparatus.

FIG. 8 illustrates an example of a use of motion data in a user authentication apparatus 800. Referring to FIG. 8, the user authentication apparatus 800 includes a motion sensor, a force sensor, and a pen pressure sensor embedded in a body 890 of the user authentication apparatus 800. For example, as shown in FIG. 8, the user authentication apparatus 800 receives a pen pressure signal 802 using the pen pressure sensor disposed at a writing end 891 of the body 890, and receives an acceleration signal 801 using the motion sensor disposed at another end of the body 890 opposite the writing end 891. Further, the user authentication apparatus 800 measures a gripping force 803 applied by the user to grip the body 890 using the force sensor, which is disposed at a portion of the body 890 to be touched with a body part, for example, a hand, of the user.

In FIG. 8, the acceleration signal 801 measured by the user authentication apparatus 800 corresponds to a tri-axial acceleration. However, the acceleration signal is not limited to a signal corresponding to a tri-axial acceleration. The acceleration signal 801 may be an acceleration with respect to multiple axes of which the number varies depending on a design. Further, the pen pressure signal 802 corresponds to a one-directional pen pressure. However, a multi-directional pen pressure may be measured. In addition, the gripping force 803 corresponds to a bi-directional force with respect to one axis. However, the gripping force 803 may correspond to a force applied to the body 890 in various directions.

The motion sensor receives at least one of the acceleration signal 801 or the pen pressure signal 802 generated with respect to the body 890 in response to a writing action of a user. The processor tracks a motion of the body 890 based on at least one of the acceleration signal 801 and the pen pressure signal 802, and estimates a signature of the user based on the tracked motion.

For example, when estimating a signature using an acceleration sensor, the processor reconstructs the signature based on a physical relationship between an acceleration of an object and a moving distance of the object. A value obtained by differentiating the moving distance two times corresponds to the acceleration of the object. Thus, inversely, the processor estimates a relative moving distance by performing integration two times with respect to the acceleration. The processor reconstructs a shape of the signature of the user by estimating the signature over time based on the estimated moving distance.

For example, as expressed by Equation 3 below, by performing integration two times with respect to the acceleration "a" determined based on the acceleration signal 801, the processor estimates a relative moving distance S of a pen tip or a portion of the object to which the acceleration sensor is attached during writing, and extracts the signature.

$$a = \frac{d^2S}{dt^2} \cdot , \cdot S = \int \left( \int a \, dt \right) dt \qquad \text{[Equation 3]}$$

The processor of the user authentication apparatus 800 detects handwriting of the user based on at least one of the acceleration signal 801, the pen pressure signal 802, and the gripping force 803 while the motion is being tracked.

The processor precisely extracts a feature point associated with the handwriting of the user based on the pen pressure signal 802. For example, although signatures are provided in the same or similar forms, a point to which a relatively great pen pressure is applied during writing varies depending on a user. The processor detects a point at which a predetermined pen pressure is applied, thereby performing precise signature identification based on writing. For example, a user A and a user B write the same signature "Samsung". Shapes of the finalized signatures of the user A and the user B are similar to each other. However, the user A applies a relatively great force when writing the letter "S", whereas the user B applies a relatively great force when writing the letter "g". The processor distinguishes between the forces through pen pressure extraction, thereby distinguishing the signature of the user A from the signature of the use B.

The processor estimates a writing posture based on at least one of the gripping force 803, the pen pressure signal 802, and a fingerprint image, and authenticates the user further based on the writing posture. For example, an individual user has a different writing posture, for example, a posture of the body 890 including an inclination of the body 890 and a posture of a finger gripping the body 890. The processor authenticates the user based on handwriting features such as a strength of a gripping force applied to grip the body 890 when the user signs, a magnitude of the pen pressure applied when the user writes a predetermined letter, and a change pattern in a magnitude of the gripping force applied while the user signs, extracted from the gripping force and the pen pressure signal. Estimation of a writing posture based on a fingerprint image will be described with reference to FIG. 9.

Figure 9:
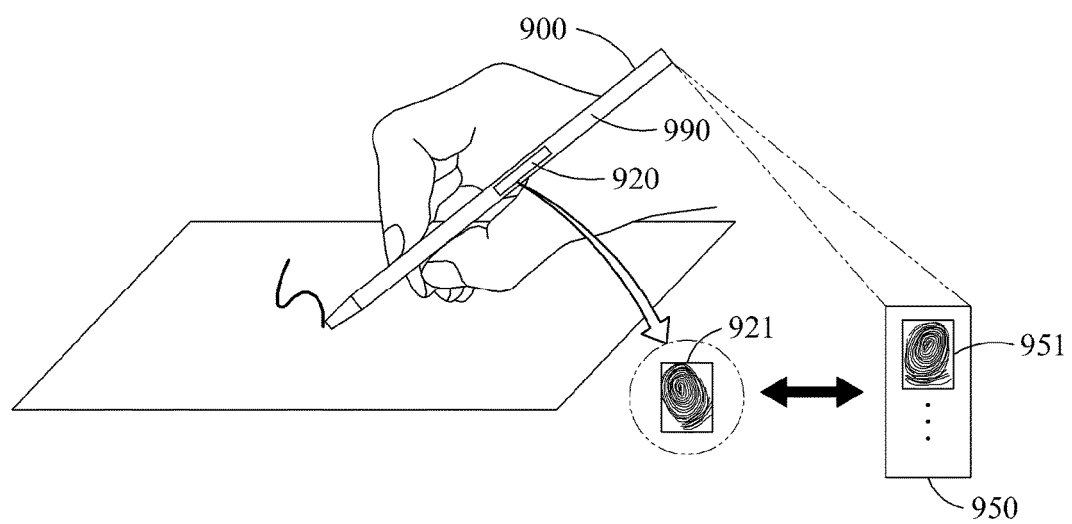
FIG. 9 illustrates an example of a use of biometric data in a user authentication apparatus.

FIG. 9 illustrates an example of a use of biometric data in a user authentication apparatus 900. Referring to FIG. 9, the user authentication apparatus 900 includes a biometric sensor 920 configured to receive biometric data from a user, as described above.

The biometric sensor 920 senses a biometric signal waveform. For example, the biometric signal waveform includes an ECG signal and/or a PPG signal. In this example, a processor verifies an identity of the user based on the sensed biometric signal waveform, and authenticates the user based on an identified signature and the verified identity. In another example, the biometric sensor 920 receives a fingerprint image from the user. The processor authenticates the user based on the received fingerprint image and the signature in response to reception of the fingerprint image being detected.

The processor authenticates the user based on the biometric signal waveform as described above, and further based on additional information included in the biometric signal waveform. For example, the processor detects a motion artifact associated with writing from the biometric signal waveform, and authenticates the user further based on the detected motion artifact. A unique characteristic is observed in a motion artifact occurring in a biometric signal waveform while an individual user writes. The processor authenticates the user based on handwriting features such as a frequency characteristic and a change pattern of the motion artifact with respect to a time.

For example, as shown in FIG. 9, the biometric sensor 920 receives a fingerprint image as biometric data from a user. The processor extracts distortion information of the fingerprint image from the fingerprint image, and authenticates the user further based on the extracted distortion information. In detail, depending on a manner that an individual user grips a body 990 of the user authentication apparatus 900, a position, an angle, and a size of a fingerprint being input into the biometric sensor 920 may change, and thus a distortion may occur in the fingerprint image. Depending on a gripping manner, a fingerprint image received from each user may include unique distortion information. Thus, the user authentication apparatus 900 authenticates the user based on the distortion information of the fingerprint image.

As shown in FIG. 9, the biometric sensor 920 receives an input fingerprint image 921 which is warped at a predetermined angle and thus includes distortion information. The processor extracts the distortion information by comparing the received fingerprint image 921 with an enrolled fingerprint image 951 stored in a memory 950. The distortion information includes a position difference, a frequency difference, a phase difference, and a size difference between the input fingerprint image 921 and the enrolled fingerprint image 951.

Figure 10:
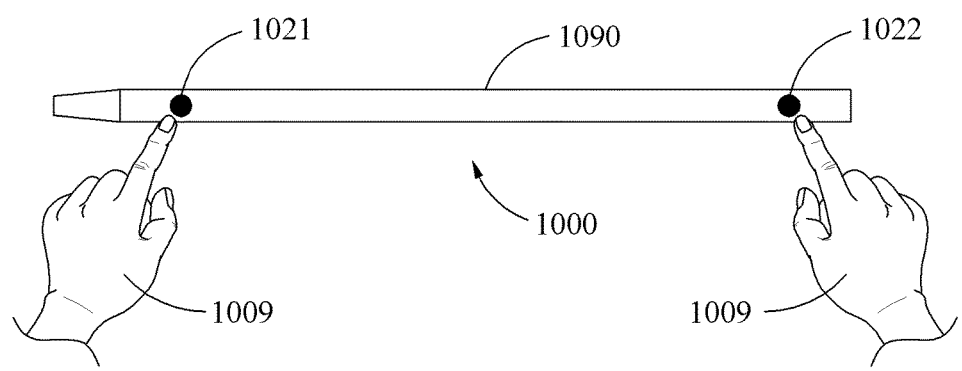
FIGS. 10 and 11 illustrate respective examples of a measuring of biometric data in a user authentication apparatus.
Figure 11:
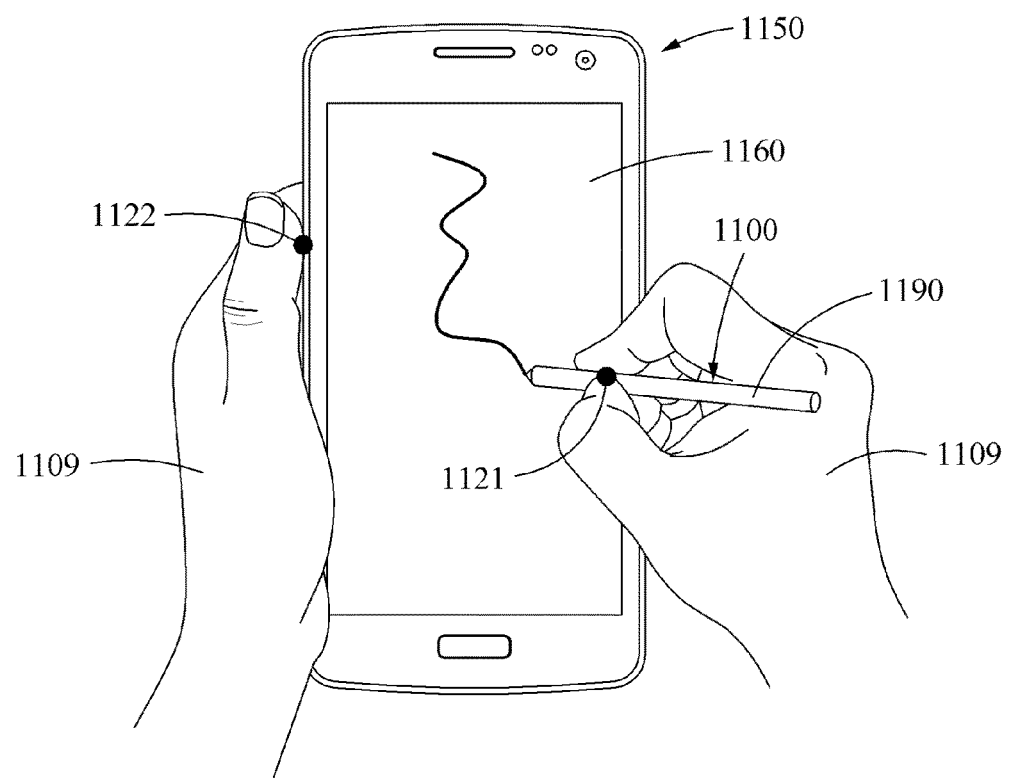

FIGS. 10 and 11 illustrate examples of a measuring of biometric data in a user authentication apparatus. As illustrated in FIGS. 10 and 11, a biometric sensor of user authentication apparatuses 1000 and 1100 receives an ECG signal. To measure an ECG signal, an electrical path passing through a heart of a user needs to be formed. For example, as shown in FIG. 10, the biometric sensor includes a first ECG sensor 1021 and a second ECG sensor 1022 on a body 1090 of the user authentication apparatus 1000. The user authentication apparatus measures an ECG signal from both hands 1009 of the user using the first ECG sensor 1021 and the second ECG sensor 1022. Since both hands are needed to measure an ECG signal, a user needs to touch the user authentication apparatus 1000 with both hands. For example, when the user touches the user authentication apparatus 1000 with both hands before or after signing, the user authentication apparatus 1000 identifies an ECG signal of the user, without using a separate additional device.

In another example, as shown in FIG. 11, a user authentication apparatus 1100 includes a first ECG sensor 1121 as a biometric sensor, and an external authentication device 1150, such as a smartphone or a tablet computer, includes a second ECG sensor 1122 as an external biometric sensor. When an electrical contact between a touch display 1160 of the external user authentication apparatus 1150 and a body 1190 of the user authentication apparatus 1100 is formed, and a user touches the external biometric sensor 1122 and the body 1190 of the user authentication apparatus 1100 with both hands 1109, respectively, an electrical path passing through a heart of the user is formed. A biometric sensor, for example, the first ECG sensor 1121, of the user authentication apparatus 1100 measures an ECG signal in response to the contact between the external biometric sensor 1122 and the body 1190 being sensed. A processor of the user authentication apparatus 1100 verifies an identity of the user based on the ECG signal measured by the external biometric sensor 1122 and the biometric sensor 1121, and authenticates the user based on an identified signature and the verified identity.

A system embodiment may include both the user authentication apparatus 1100 and the external authentication device 1150. For example, the processor of the user authentication apparatus 1100 may communicate with the external authorization device 1150 to authenticate the user to use additional features and capabilities of the external authentication device 1150. More specifically, the user may be authenticated to use the external authentication device 1150 based on a result of the authentication of the user based on the received identification information (e.g., the identified signature and the verified identity).

Figure 12:
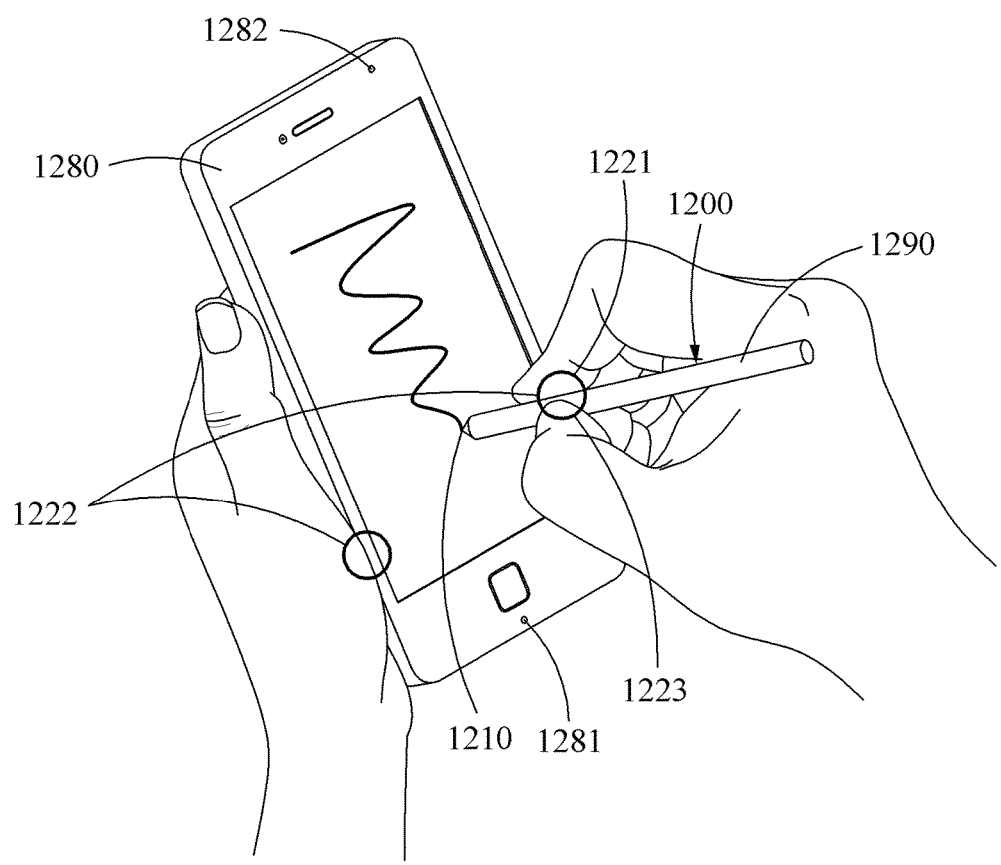
FIG. 12 illustrates an example of a use of an external authentication device in combination with a user authentication apparatus.

FIG. 12 illustrates an example of use of an external authentication device 1280 in combination with a user authentication apparatus 1200. The user authentication apparatus 1200 interoperates with an identification solution embedded in an external authentication device 1280, such as a smartphone or a tablet computer, through a communicator embedded in the user authentication apparatus 1200. When authentication is requested in the external authentication device 1280, for example, when an application requiring authentication is executed in a smart phone, the user authentication apparatus 1200 performs signature identification 1210 and a variety of biometric identifications. In this example, the external authentication device 1280 performs face identification 1282 using an embedded front camera, and voice identification 1281 using an embedded microphone.

For example, while the user writes with the body 1290 of the user authentication apparatus 1200, the user authentication apparatus 1200 performs signature identification 1210, fingerprint identification 1221, ECG identification 1222, and PPG identification 1223, and the external authentication device 1280 performs the voice identification 1281 and the face identification 1282. The user authentication apparatus 1200 may provide an authentication solution having a relatively high security level by combining identification results. In this example, the user authentication apparatus comprehensively utilizes the identifications, and assigns a weight to a situation with respect to each identification result.

A system embodiment may include both the user authentication apparatus 1200 and the external authentication device 1280. For example, the processor of the user authentication apparatus 1200 may communicate with the external authorization device 1280 to authenticate the user to use additional features and capabilities of the external authentication device 1280. More specifically, the user may be authenticated to use the external authentication device 1280 based on a result of the authentication of the user based on the received identification information (e.g., the identified signature and the biometric identifications).

In addition to the embedded signature identification and the variety of biometric identifications, the user authentication apparatus 1200 performs an additional identification based on data collected through interoperation with the neighboring external authentication device 1280, or receives an additional identification result, thereby increasing a security level and authentication accuracy.

Figure 13:
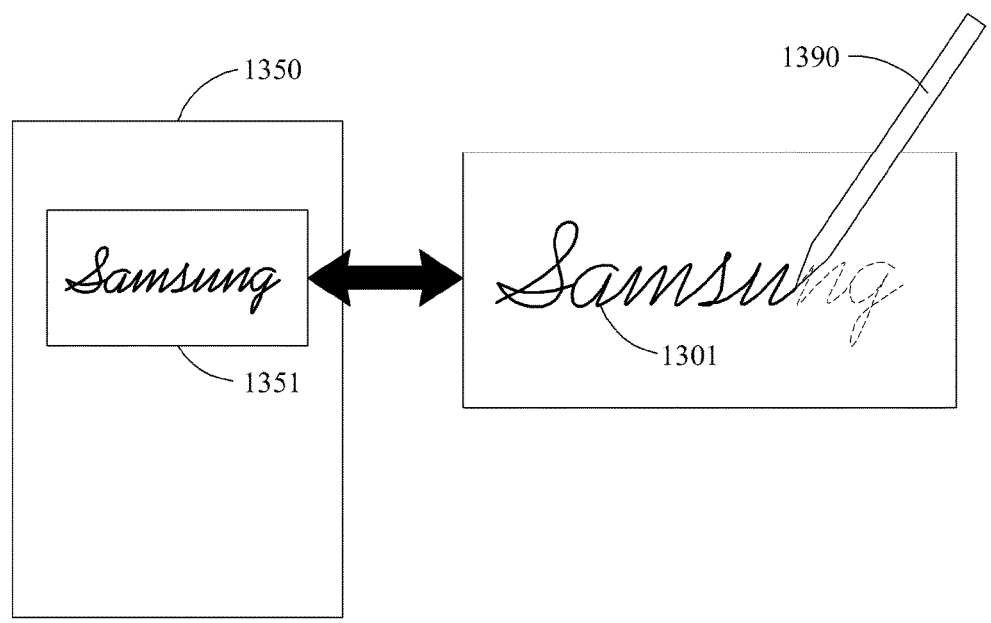
FIG. 13 illustrates an example of an authenticating of a signature being controlled to be performed in a user authentication apparatus.

FIG. 13 illustrates an example of an authenticating of a signature being controlled to be performed in a user authentication apparatus 1390. A motion sensor of the user authentication apparatus 1390 tracks a motion of the user authentication apparatus 1390, and a processor of the user authentication apparatus 1390 detects a handwriting feature while the motion is being tracked, identifies a signature of a user based on the tracked motion, and authenticates the user based on the identified signature and the detected handwriting feature.

For example, the processor detects the handwriting feature based on at least one of an acceleration of the user authentication apparatus 1390, a pen pressure, a gripping force applied by the user to grip the user authentication apparatus 1390, and biometric data of the user. The processor authenticates the user by estimating at least a portion 1301 of the signature while tracking the motion of the user authentication apparatus 1390 in real time, and comparing the portion 1301 of the signature with a corresponding portion in an enrolled signature 1351 stored in a database of a memory 1350.

The apparatuses, units, modules, devices, and other components illustrated in FIGS. 3-5, 11 and 12 (e.g., the motion sensor 310, the biometric sensor 320, the processor 330, the communicator 440, the memory 550, and similar devices and components described throughout the disclosure) that perform the operations described herein with respect to FIGS. 6-13 are implemented by hardware components. Examples of hardware components include controllers, sensors, generators, drivers, memories, comparators, arithmetic logic units, adders, subtractors, multipliers, dividers, integrators, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 6-13. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 6 and 7 that perform the operations described herein with respect to FIGS. 3-5, 11 and 12 are performed by computing hardware, for example, by one or more processors or computers, as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A user authentication apparatus, comprising:
    a motion sensor configured to receive motion data associated with a motion of a body of the user authentication apparatus;
    a biometric sensor configured to obtain, when a biosignal is measured by the biometric sensor, biometric data from the biosignal, associated with a user of the user authentication apparatus; and
    a processor configured to:
        identify a signature of the user based on the motion data; and
        authenticate the user based on the identified signature when the biosignal is determined to not be measured, and authenticate the user based on the identified signature and the biometric data when the biosignal is determined to be measured.

2. The user authentication apparatus of claim 1, wherein the processor is further configured to:
    verify an identity of the user based on the biometric data in response to the biometric data by the biometric sensor being measured; and
    authenticate the user based on the identified signature and the verified identity.

3. The user authentication apparatus of claim 1, wherein the motion sensor is further configured to sense a start of a writing action of the user, and collect motion data associated with a motion corresponding to the writing action.

4. The user authentication apparatus of claim 1, wherein:
the motion sensor is further configured to receive at least one of an acceleration signal and a writing pressure signal generated with respect to the body in response to a writing action of the user; and
the processor is further configured to track a motion of the body based on at least one of the acceleration signal and the writing pressure signal, and estimate the signature of the user based on the tracked motion.

5. The user authentication apparatus of claim 4, further comprising:
a force sensor configured to sense a gripping force used to grip the body,
wherein the processor is further configured to detect a handwriting action of the user based on at least one of the acceleration signal, the writing pressure signal, or the gripping force while the motion is being tracked.

6. The user authentication apparatus of claim 1, wherein the processor is further configured to:
estimate a writing posture based on at least one of a gripping force applied by the user to grip the body, a writing pressure, or a fingerprint image; and
authenticate the user further based on the writing posture.

7. The user authentication apparatus of claim 1, wherein the biometric sensor is further configured to sense for biometric signal waveform from the user; and
the processor is further configured to distinguish a motion artifact in a result of the sensing from the biometric signal waveform, and authenticate the user further based on the detected motion artifact.

8. The user authentication apparatus of claim 7, wherein the biometric signal waveform is an electrocardiogram (ECG) signal or a photoplethysmograph (PPG) signal.

9. The user authentication apparatus of claim 1, wherein:
the biometric sensor is further configured to receive a fingerprint image from the user; and
the processor is further configured to extract distortion information of the fingerprint image from the fingerprint image, and authenticate the user further based on the extracted distortion information.

10. The user authentication apparatus of claim 1, wherein:
the biometric sensor is further configured to sense a biometric signal waveform comprising at least one of an electrocardiogram (ECG) signal or a photoplethysmograph (PPG) signal; and
the processor is further configured to verify an identity of the user based on the sensed biometric signal waveform, and authenticate the user further based on the verified identity.

11. The user authentication apparatus of claim 1, wherein:
the biometric sensor is further configured to measure an electrocardiogram (ECG) signal using an external biometric sensor and the biometric sensor in response a contact between the external biometric sensor and the body being sensed; and
the processor is further configured to verify an identity of the user based on the measured ECG signal, and authenticate the user further based on the verified identity.

12. The user authentication apparatus of claim 1, wherein:
the biometric sensor is further configured to receive a fingerprint image from the user; and
the processor is configured to authenticate the user further based on the received fingerprint image and the signature in response to reception of the fingerprint image being detected.

13. The user authentication apparatus of claim 1, further comprising:
a communicator configured to communicate with an external authentication device,
wherein the processor is further configured to receive identification information associated with at least one of a body part or a voice of the user from the external authentication device through the communicator in response to the external authentication device being available, and authenticate the user further based on the received identification information.

14. The user authentication apparatus of claim 1, further comprising:
a communicator configured to receive at least one of a face image or voice data from an external authentication device,
wherein the processor is configured to authenticate the user further based on at least one of the face image or the voice data.

15. The user authentication apparatus of claim 1, wherein:
the processor is further configured to apply a weight to at least one of an identification result obtained based on the signature, an identification result obtained based on the biometric data, or an identification result obtained by an external authentication device, and authenticate the user further based on the at least one identification result having the weight applied thereto.

16. The user authentication apparatus of claim 15, wherein:
the processor is further configured to determine the weight with respect to each of the identification results based on accuracies of the signature, the biometric data, or a signal received from the external authentication device.

17. A user authentication method, comprising:
receiving motion data associated with a motion of a body of a user authentication apparatus;
receiving biometric data associated with a user of the authentication apparatus, when the biometric data is detected;
identifying a signature of the user based on the motion data; and
authenticating the user based on the identified signature when the biometric data is determined to not be detected, and authenticating the user based on the identified signature and the biometric data when the biometric data is determined to be detected.

18. A non-transitory computer-readable storage medium comprising programmed instructions configured to cause a computer to perform the method of claim 17.

19. A user authentication apparatus, comprising:
a motion sensor configured to track a motion of the user authentication apparatus;
a biometric sensor configured to obtain, when a biosignal is measured by the biometric sensor, biometric data from the biosignal, associated with a user of the user authentication apparatus; and
a processor configured to:
detect a handwriting feature while the motion is being tracked;
identify a signature of the user of the user authentication apparatus based on the tracked motion; and
authenticate the user based on the identified signature when the biosignal is determined to not be measured, and authenticate the user based on the identified signature, the detected handwriting feature, and the biometric data when the biosignal is determined to be measured.

20. The user authentication apparatus of claim 19, wherein the processor is further configured to detect the handwriting feature based on at least one of an acceleration of the user authentication apparatus, a writing pressure, a gripping force applied by the user to grip the user authentication apparatus, or biometric data of the user.

21. The user authentication apparatus of claim 19, wherein the processor is further configured to:
estimate at least a portion of the signature while tracking the motion in real time; and
authenticate the user by comparing the portion of the signature to a corresponding portion of an enrolled signature stored in a database.

22. A writing instrument, comprising:
a motion sensor configured to receive motion data associated with a motion of a body of the writing instrument while a user performs a writing action with the writing instrument;
a biometric sensor configured to obtain, when a biosignal is measured by the biometric sensor, biometric data from the biosignal, associated with the user;
a pressure sensor configured to detect a writing pressure signal generated in response to the writing action; and
a processor configured to:
identify a signature of the user based on the motion data and the writing pressure signal; and
authenticate the user based on the identified signature when the biosignal is determined to not be measured, and authenticate the user based on the identified signature and the biometric data when the biosignal is determined to be measured.

23. The writing instrument of claim 22, wherein the detecting of the writing pressure signal comprises detecting points at which a predetermined writing pressure is applied.

24. The writing instrument of claim 23, wherein the processor is further configured to distinguish the identified signature from another signature having a form that is similar to a form of the identified signature, based on the detecting of the points at which the predetermined pressure is applied.

25. The writing instrument of claim 22, wherein the processor is further configured to identify the user based on the biometric data received from the biometric sensor.

* * * * *